United States Patent
Levi

(10) Patent No.: US 7,347,205 B2
(45) Date of Patent: Mar. 25, 2008

(54) METHOD FOR USE WITH THE PRESSURE TRIGGERING OF MEDICAL VENTILATORS

(75) Inventor: Andrew P. Levi, Madison, WI (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 11/216,619

(22) Filed: Aug. 31, 2005

(65) Prior Publication Data

US 2007/0044798 A1    Mar. 1, 2007

(51) Int. Cl.
*A61M 16/00*    (2006.01)
*A62B 7/00*    (2006.01)

(52) U.S. Cl. ............... 128/204.18; 128/204.21; 128/204.23

(58) Field of Classification Search ........... 128/204.18, 128/204.21, 204.23
See application file for complete search history.

(56) References Cited

U.S. PATENT DOCUMENTS 5,148,802 A * 9/1992 Sanders et al. ........ 128/204.18
5,438,980 A * 8/1995 Phillips ................. 128/204.23
5,492,113 A * 2/1996 Estes et al. ............ 128/204.23
5,503,146 A * 4/1996 Froehlich et al. ...... 128/204.23
6,968,842 B1 * 11/2005 Truschel et al. ....... 128/204.18

* cited by examiner

*Primary Examiner*—Justine R. Yu
*Assistant Examiner*—Kristen C. Matter
(74) *Attorney, Agent, or Firm*—Andrus, Sceales, Starke & Sawall, LLP

(57) ABSTRACT

A method for providing a pressure reference level for pressure triggering a ventilator responsive to a spontaneous breathing attempt by a patient. In the method, the patient connection of the breathing circuit is capped or plugged. A gas flow is then provided through the breathing circuit and is altered to an amount that causes the flow resistance properties of the breathing circuit to generate a desired gas pressure in the breathing circuit suitable for use as a reference pressure by the ventilator for pressure responsive triggering. During the operation of the ventilator, gas flow in a corresponding amount serves as a bias flow in the breathing circuit to assist breathing by the patient. The bias flow also generates the reference pressure level in the breathing circuit. A reduction in pressure from the pressure level resulting from inhalation by the patient triggers the operation of the ventilator.

7 Claims, 2 Drawing Sheets

METHOD FOR USE WITH THE PRESSURE TRIGGERING OF MEDICAL VENTILATORS

BACKGROUND OF THE INVENTION

The present invention relates to establishing a reference pressure level for use in triggering the operation of a medical ventilator supplying breathing gases to a patient. Through use of the invention, the operation of the ventilator in supporting spontaneous breathing efforts by the patient may be enhanced.

Patients in need of respiratory assistance are often placed on a mechanical ventilator. A mechanical ventilator is a device that provides breathing gas to a patient who is unable to breath, or alternatively, detects a patient's attempt to breathe and provides breathing gases to assist in that effort. The breathing gases typically comprise air, or air mixed with other gases, such as additional oxygen. The breathing gases are delivered to the patient from the ventilator via flexible tubes comprising the patient breathing circuit.

The patient breathing circuit comprises an inspiratory limb which supplies the breathing gases to the patient from the ventilator and an expiratory limb which directs the expired gases away from the patient. Gas flow is facilitated by a Y-connector for the inspiratory limb and expiratory limb and for a patient limb or connector leading from the Y-connector to the patient. A plurality of one way check valves in the breathing circuit direct gas flows in the breathing circuit. A patient interface, such as a face mask or endotracheal tube, administers the breathing gases from the breathing circuit to the patient. Flow sensors and pressure transducers are placed in the breathing circuit to monitor the delivery of breathing gases for safety and control purposes.

In some situations, such as those found in critical care units, emergency rooms, or operating rooms, a patient may be spontaneously breathing yet be too weak or sedated to carry out sufficient respiratory activity by himself/herself. Or, the respiratory system of the patient may be injured or too inefficient for adequate respiration. In these instances, the patient may start an inspiration of breathing gases but is not able to overcome the resistance to the flow of breathing gases in the breathing circuit to continue a full respiratory cycle. The mechanical ventilator is then used to assist the patient in breathing. This assistance is provided by delivering breathing gases to fill the lungs with breathing gases. At the end of the mechanical assistance, the supply of breathing gas to the patient terminates and the natural compliance of the patient's chest wall forces the breathing gases out of the lungs in an expiration, thus completing a mechanically assisted respiratory cycle.

An analogous situation occurs when weaning a patient receiving mechanical ventilation off the ventilator to a state of spontaneous breathing.

When assisting the breathing of a patient, the mechanical ventilator delivers breathing gases to the patient when a patient breathing attempt is detected. This detection is typically accomplished by using sensors in the breathing circuit to detect changes in conditions in the breathing circuit as the patient attempts to inhale. It is desirable to make the initiation, or "triggering" of ventilation sensitive, or responsive, to the breathing attempts of the patient as a patient being mechanically ventilated is often in a weakened condition and the patient's spontaneous breathing attempts while requiring a relatively large amount of inspiratory work on the part of the patient may not produce much of a change in conditions in the breathing circuit.

In the past, flow sensing has been generally recognized as providing a more sensitive triggering action. This is due to the fact a pressure level to serve as a reference for a pressure triggering action has been difficult to establish with the necessary degree of accuracy.

SUMMARY OF THE INVENTION

The present invention is one that enables sensitive pressure triggering of a mechanical ventilator, responsive to spontaneous breathing attempts by a patient, to be carried out by providing an accurate pressure reference level for the pressure triggering action of a ventilator responsive to the spontaneous breathing attempt.

In the method, gas flow in the patient connection of the breathing circuit is limited, preferably by capping or plugging the patient connection. A flow of gas is then provided through the breathing circuit. The gas flow is established at an amount that causes the flow resistance properties of the breathing circuit to generate a desired gas pressure in the breathing circuit suitable for use as a reference pressure by the ventilator for pressure responsive triggering. The gas flow in the breathing circuit may be altered until the desired gas pressure is generated.

During the operation of the ventilator, gas flow in a corresponding amount serves as a bias flow in the breathing circuit to assist breathing by the patient. The bias flow also generates the reference pressure level in the breathing circuit. A reduction in breathing circuit pressure from the reference pressure level, caused by the commencement of inhaling by the patient, trigger operation of the ventilator.

The advantages of this invention include increased sensitivity of the pressure based detection of spontaneous patient breathing attempts. The invention also eliminates the need for additional flow sensors in the patient breathing circuit for triggering purposes, thus providing a more economical design.

DETAILED DESCRIPTION

Figure 1:
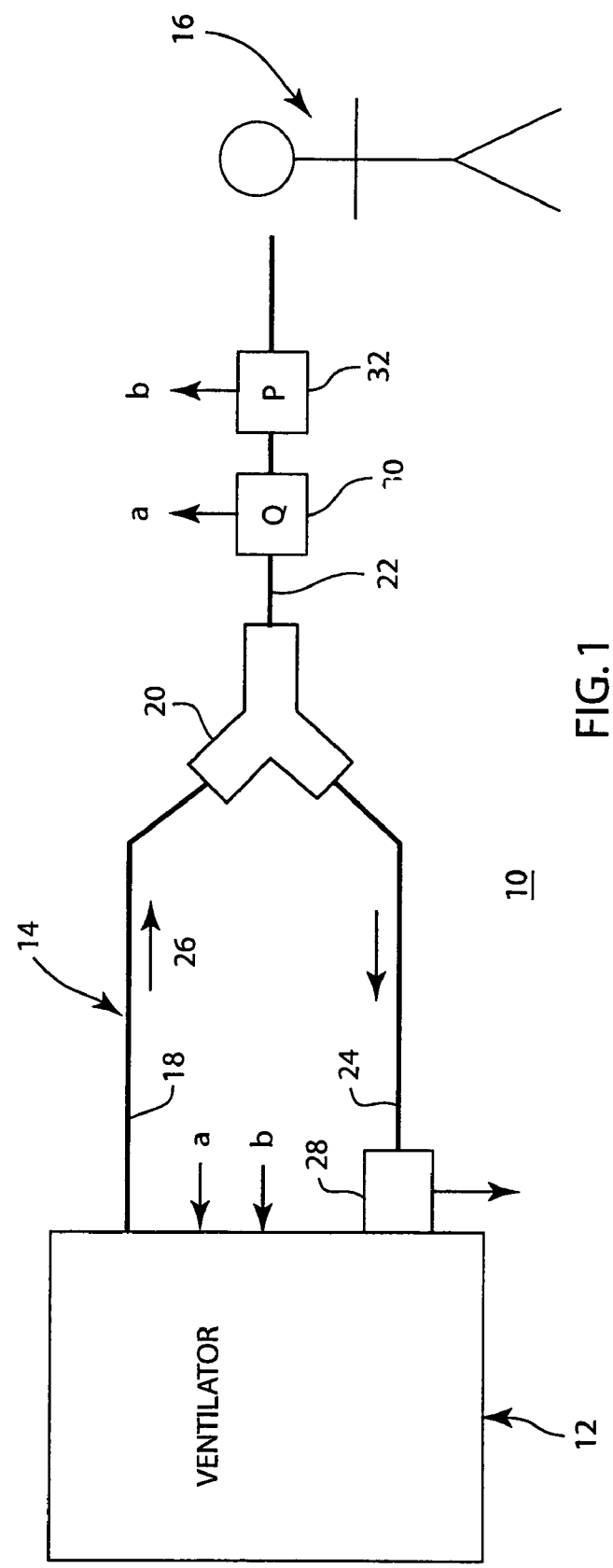
FIG. 1 is a schematic diagram of a mechanical ventilation system for a patient.

Referring now to the figures, FIG. 1 is a schematic diagram depicting a mechanical ventilator system 10 for use with the method of the present invention. The mechanical ventilator system comprises mechanical ventilator 12 and patient breathing circuit 14. Breathing circuit 14 is connected in gas communication with patient 16.

The patient breathing circuit 14 comprises an inspiratory limb 18, a Y-connector 20, a patient limb or connection 22 and an expiratory limb 24. Breathing gases from ventilator 12 flow in the direction of arrow 26 through the inspiratory limb 18 and Y-connector 20 to the patient via the patient limb 22 during inspiration. The breathing gases may be supplied to patient 16 by a respiratory mask, tent, endotracheal tube, nasal cannula, or other suitable device. The patient's expiratory breathing gases travel through patient limb 22, Y-connector 20, and expiratory limb 24 for return to an exhaust port 28 on the ventilator 12. One-way check valves (not pictured) within the breathing circuit to ensure that gas flow travels in the desired path.

Mechanical ventilator 12 also provides a constant bias flow of breathing gases in breathing circuit 14. This bias flow facilitates the mechanical ventilation as well as the patient's breathing action.

Breathing circuit 14 includes one or more flow sensors 30 and pressure transducers 32 connected to ventilator 12 for monitoring and control purposes. The sensors are shown in patient limb 22 for illustrative purposes but may be located elsewhere in the breathing circuit, as for example in Y-connector 20. The attempts of patient 16 to spontaneously breathe may also be detected by the use of flow sensors and/or pressure transducers. A flow sensor 32 will detect changes in gas flow amount or direction responsive to an inhalation and has been commonly used to trigger the operation of ventilator 12. A pressure transducer will detect a reduction in the pressure of the breathing circuit indicative of the commencement of an inhalation.

Gas flows in the breathing circuit pass through the pneumatic resistance of the breathing circuit creating a pressure drop in the circuit. As noted above, it has heretofore been difficult to obtain accurate pressure triggering for a mechanical ventilator due to the absence of accurate pressure level from which a pressure reduction in the breathing circuit indicative of spontaneous breathing by the patient can be referenced for triggering purposes.

Figure 2:
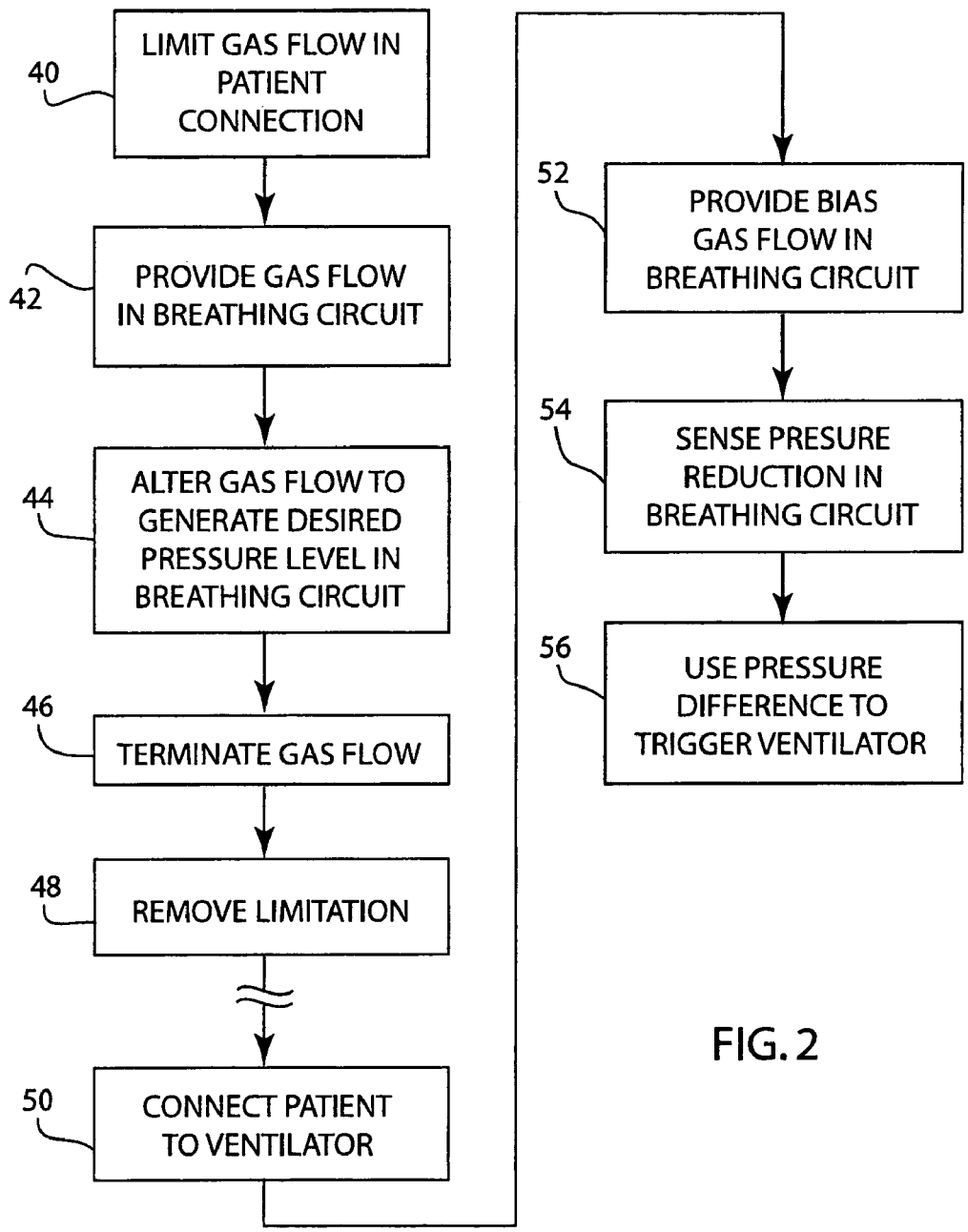
FIG. 2 is a flow chart depicting the steps of the present invention.

The flow chart of FIG. 2 describes the method of the present invention by which such a pressure reference level may be accurately established, thereby to obtain sensitive pressure triggering for the ventilator. In step 40, a clinician attending patient 16 limits gas flow in the connection of breathing circuit 14 to patient 16. This may be accomplished by removing the patient interface means from patient limb 22 and placing a removable plug in the end of the patient limb or placing a removable cap over the end of the patient limb to occlude the patient limb. Next, in step 42, a gas flow is provided to patient breathing circuit 14, typically via inspiration limb 18. This gas flow will flow through the resistance of breathing circuit 14 and create a pressure in the breathing circuit. Since the gas flows through the entire breathing circuit, except for the patient limb, essentially all of the resistance of the breathing circuit is accounted for. The pressure may be sensed by pressure transducer 32. The amount of gas flow is altered until that which generates a desired level of pressure in the breathing circuit is provided to breathing circuit 14. The desired pressure level is preferably selected to a level less than or equal to the minimum trigger level for ventilator 12. This is typically less than or equal to 0.1 cmH$_2$O.

Thereafter the gas flow is terminated, and the plug or cap is removed, at steps 46 and 48.

In the mechanical ventilation of patient 16, the patient interface means is applied to the patient at step 50 to connect the patient to the breathing circuit and ventilator. Ventilator 12 provides a bias gas flow in the breathing circuit in step 52 corresponding in amount to that which generated the desired gas pressure in the breathing circuit in step 44. This bias gas flow is provided at least during the end of exhalation by patient 16 and is typically provided during both exhalation and inhalation. The generated pressure, which has been accurately established by the method steps 40 through 48 and 52, serves a pressure reference level for the pressure triggering action of ventilator 12. As patient 16 starts to inhale in a spontaneous breath, a pressure reduction from the generated pressure reference level will be sensed by pressure sensor 32 and the resulting pressure difference caused by the pressure reduction used to trigger operation of ventilator 12 in step 56. Due to the accurate establishment of the reference pressure level, the triggering action can be accurately and sensitively carried out.

Various alternatives and embodiments are contemplated as being within the scope of the following claims particularly pointing out and distinctly claiming the subject matter regarded as the invention.

What is claimed is:

1. A method for providing a reference pressure level for the pressure responsive triggering of a mechanical ventilator to assist a spontaneously breathing effort by a patient, a breathing circuit for the ventilator having a gas flow path extending from the ventilator to an exhaust port and along which breathing gases flow through the breathing circuit, the breathing circuit having a patient connection interposed along the gas flow path of the breathing circuit downstream from the ventilator and upstream from the exhaust port, said method comprising the steps of:

configuring the breathing circuit to dispose at least one pressure transducer along the gas flow path:

limiting the gas flow properties of the patient connection while maintaining gas flow properties in the gas flow path of the breathing circuit;

providing a gas flow along the gas flow path of the breathing circuit from the ventilator to the exhaust port;

sensing the gas pressure generated in the breathing circuit by the gas flow along the gas flow path and through the flow resistance of the gas flow path with the pressure transducer disposed along the gas flow path; and ascertaining when the gas flow along the gas flow path is in an amount sufficient to cause the flow resistance properties of the gas flow path of the breathing circuit to generate a desired gas pressure in the breathing circuit suitable for use as a reference pressure level for the pressure responsive triggering action, gas flow in a corresponding amount serving as a bias flow through the gas flow path of the breathing circuit in the subsequent operation of the ventilator.

2. A method according to claim 1 wherein the gas flow providing step is further defined as:

flowing gas along the gas flow path of the breathing circuit; and altering the gas flow in the breathing circuit to an amount that attains the desired gas pressure level in the breathing circuit.

3. A method according to claim 1 wherein the step of limiting the gas flow in the patient connection is further defined as occluding the patient connection.

4. A method according to claim 1 further defined as providing a gas flow along the gas flow path of the breathing circuit sufficient to generate a gas pressure less than or equal to a minimum pressure triggering level for operation of the ventilator.

5. A method according to claim 1 further defined as providing a gas flow along the gas flow path of the breathing circuit sufficient to generate a gas pressure in the breathing circuit less than or equal to 0.1 cmH$_2$O.

6. A method according to claim 1 further including the steps of:

removing the limitation to the gas flow properties in the patient connection after generating the desired gas pressure; and supplying a bias gas flow from the ventilator in the breathing circuit corresponding to the amount of gas flow that generated the desired gas pressure.

7. A method according to claim 6 wherein a spontaneous breathing attempt by the patient causes a reduction in pressure in the breathing circuit which is used to trigger operation of the ventilator, wherein the method includes the step of sensing the reduced pressure resulting from a spontaneous breathing attempt, and wherein the reference pressure level is used to establish a pressure difference between the reference level and the reduced pressure that is used to trigger operation of the ventilator.

* * * * *